United States Patent [19]
Haddleton et al.

[11] Patent Number: 5,962,609
[45] Date of Patent: *Oct. 5, 1999

[54] FREE RADICAL POLYMERISATION PROCESS

[75] Inventors: David Mark Haddleton, Kenilworth; Andrew Victor Graham Muir, Guilford; Stephen William Leeming, Flixton; John Patrick O'Donnell, Runcorn; Stuart Nicholas Richards, Norley, all of United Kingdom

[73] Assignee: Zeneca Limited, London, United Kingdom

[ * ] Notice: This patent is subject to a terminal disclaimer.

[21] Appl. No.: 08/836,378
[22] PCT Filed: Oct. 9, 1995
[86] PCT No.: PCT/GB95/02376
§ 371 Date: Jul. 15, 1997
§ 102(e) Date: Jul. 15, 1997
[87] PCT Pub. No.: WO96/13527
PCT Pub. Date: May 9, 1996

[30] Foreign Application Priority Data

Oct. 28, 1994 [GB] United Kingdom .................... 9421771
Apr. 28, 1995 [GB] United Kingdom .................... 9508625

[51] Int. Cl.$^6$ .................................. C08F 2/38; C07F 5/02
[52] U.S. Cl. .......................... 526/131; 526/133; 526/172; 526/328; 556/7; 556/138
[58] Field of Search .................................. 526/131, 133, 526/172, 328; 556/7, 138

[56] References Cited

U.S. PATENT DOCUMENTS

| | | |
|---|---|---|
| 4,526,945 | 7/1985 | Carlson et al. . |
| 4,680,354 | 7/1987 | Lin et al. . |
| 4,694,054 | 9/1987 | Janowicz .................................... 526/93 |
| 5,770,665 | 6/1998 | Haddleton et al. ...................... 526/131 |

FOREIGN PATENT DOCUMENTS

| | | |
|---|---|---|
| 0 196 783 | 10/1986 | European Pat. Off. .......... C08F 2/28 |
| 199 436 | 10/1986 | European Pat. Off. . |
| WO 87/03605 | 6/1987 | WIPO ............... C08F 4/30 |
| 95/04759 | 2/1995 | WIPO . |
| 95/04767 | 2/1995 | WIPO . |
| 95/17435 | 6/1995 | WIPO . |
| 95/27737 | 10/1995 | WIPO . |

OTHER PUBLICATIONS

Enikolopayan et al, J. Polym. Sc. Polymer Chem. Ed., vol. 19, 879 (1981).

Primary Examiner—Donald R. Wilson
Attorney, Agent, or Firm—Pillsbury Madison & Sutro LLP

[57] ABSTRACT

Process for the free-radical polymerisation of olefinically unsaturated monomer(s) using a free-radical initiator, the polymerisation being performed in the presence of a compound for effecting molecular weight control, wherein the molecular weight control compound is a Co II chelate of the following formula I

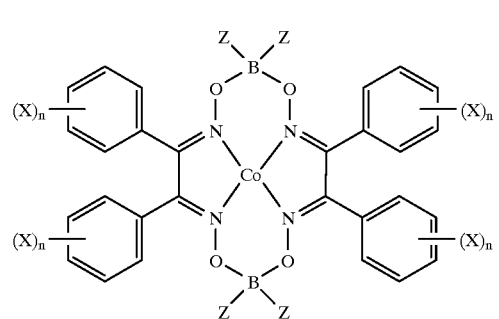

wherein each group X, independently in each ring and in different rings, is a substituent selected from alkyl of 1 to 14 carbon atoms and cycloalkyl of 6 to 14 carbon atoms; n, independently in each ring, is 0 to 5 provided that in at least one ring, n is 1 to 5; Z, independently on each boron atom, is selected from F, Cl, Br, OH, alkoxy of 1 to 12 carbon atoms, aryloxy of 6 to 12 carbon atoms, alkyl of 1 to 12 carbon atoms, and aryl of 6 to 12 carbon atoms; or two Z groups taken together provide on one or both boron atoms a group —O—(Q)—O— where Q is a divalent aryl or alicyclic linking group or an alkylene linking group, or two Z groups taken together on one or both boron atoms provide a 1,5-cyclooctanediyl linking group; or being a Co III analogue of said Co II chelate of formula I in which the Co atom is additionally covalently bonded, in a direction at right angles to the macrocyclic chelate ring system, to H, halide or other anion, or a homolytically dissociable organic group; and wherein optionally at least one further ligand is coordinated to the CoII or CoIII atom, being a ligand which does not alter the Co valency state. Also the Co chelates used in the polymerisation process, a process for their production, and the use in various applications of oligomers made using the polymerisation process.

44 Claims, No Drawings

FREE RADICAL POLYMERISATION PROCESS

The present invention relates to a process for the free-radical initiated polymerisation of olefinically unsaturated monomer(s) in which molecular weight control is achieved by the presence of certain cobalt chelate complexes. The invention also relates to the cobalt chelate complexes themselves and to a process for their production.

Polymers of low molecular weight, known as oligomers, are often desired for various applications (such as coating compositions) either in their own right or as precursors for other polymers. In order to form oligomers it is necessary to appropriately control the polymerisation process being used to yield the desired type of product. In free-radical polymerisations, which are widely used for polymerising olefinically unsaturated monomers, various conventional means are employed for controlling and limiting the molecular weight of the growing polymer chains. Of these, the addition of thiol compounds to the polymerisation has probably been used the most extensively; the thiol acts as an effective chain transfer agent but unfortunately contaminates the system to which it has been added by virtue of its distinctive and persistent odour.

More recently, attention has turned to the use of various transition metal complexes, particularly cobalt chelate complexes, as chain transfer agents for use in controlling molecular weight when radically polymerising olefinically unsaturated monomers.

For example, various literature references, such as N. S.Enikolopyan et al, J.Polym.Sci., Polym. Chem. Ed., Vol 19, 879 (1981), disclose the use of cobalt II porphyrin complexes as chain transfer agents in free radical polymerisation, while U.S. Pat. No. 4,526,945 discloses the use of dioxime complexes of cobalt II for such a purpose. Various other publications, e.g. U.S. Pat. No. 4,680,354, EP-A-0196783 and U.S. Pat. No. 4,694,054, describe the use of certain other types of cobalt II chelates as chain transfer agents for the production of oligomers of olefinically unsaturated monomers by free-radical polymerisation. WO-A-87/03605 on the other hand claims the use of certain cobalt III chelate complexes for such a purpose. Whether or not a particular cobalt chelate complex (or class of cobalt chelate complexes) is effective as a chain transfer agent in a radical polymerisation process is unpredictable; some are effective and some are not.

We have now discovered that molecular weight control in the free-radical polymerisation of olefinically unsaturated monomers may be effectively achieved with a further class of cobalt chelate complexes which have not been disclosed in the prior art.

According to the present invention there is provided a process for the free-radical polymerisation of olefinically unsaturated monomer(s) (especially methacrylate monomer (s)) using a free-radical initiator, the polymerisation being performed in the presence of a compound for effecting molecular weight control, the molecular weight control compound being a CoII chelate of the following formula I:

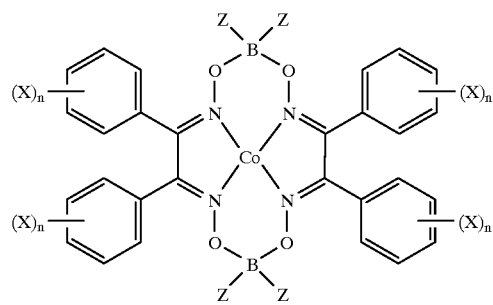

wherein each group X, independently in each ring and in different rings, is a substituent selected from alkyl of 1 to 14 carbon atoms and cycloalkyl of 6 to 14 carbon atoms; n, independently in each ring, is 0 to 5 provided that in at least one ring, n is 1 to 5; Z, independently on each boron atom, is selected from F, Cl, Br, OH, alkoxy of 1 to 12 carbon atoms, aryloxy of 6 to 12 carbon atoms, alkyl of 1 to 12 carbon atoms, and aryl of 6 to 12 carbon atoms;

or two Z groups taken together provide on one or both boron atoms a group —O—(Q)—O— where Q is a divalent aryl or alicyclic linking group or an alkylene linking group, or two Z groups taken together on one or both boron atoms provide a 1,5-cyclooctanediyl linking group;

or being a CoIII analogue of said CoII chelate of formula I in which the Co atom is additionally covalently bonded, in a direction at right angles to the macrocyclic chelate ring system, to H, halide or other anion, or a homolytically dissociable organic group; and wherein optionally at least one further ligand is coordinated to the Co II or Co III atom, being a ligand(s) which does not alter the Co valency state.

Preferably X is alkyl of 1 to 14 carbon atoms, and may be straight-chained or branched if the option arises. More preferably X is alkyl of 1 to 4 carbon atoms and particularly is methyl.

It is possible for n (representing the number of substituents in a ring) to be 0 in a ring(s) (i.e. the ring is unsubstituted) provided that in at least one ring n is 1 to 5. Preferably, n is 1 to 5 in at least two rings and more preferably is 1 to 5 in at least three rings and in particular is 1 to 5 in all four rings.

Preferably n is 1 to 3 in a substituted ring, more preferably being 1 or 2.

Preferably, when n is 1 to 3 in a substituted ring it has the same value in each ring (if more than one ring is substituted), and more preferably is 1 or 2, and particularly is 1 in each substituted ring.

When n=2, the substituents are preferably in the 3,4 or 2,4 positions.

When n=1, the substituent may be in the 2,3 or 4 positions of a ring, preferably being at the same position in all substituted rings. It is particularly preferred that the substituent is at the 2, 3 or 4 position of all four rings, and especially at the 4 position of all four rings.

The groups Z are preferably all the same (or when taken together to form a divalent group such groups are the same on both boron atoms) and more preferably are all F.

When both Z groups together provide a group —O—(Q)—O— where Q is a divalent aryl or alicyclic linking group, the group Q preferably has 6 to 10 carbon atoms and in such cases linkage is from adjacent ring carbon atoms;

more preferably Q is o-phenylene or 1,2-cyclohexanediyl. Where Q is alkylene it preferably has the formula —$(CR^1_2)_m$ where each $R^1$ is independently hydrogen or $C_xH_{2x+1}$ where x is 1 to 12 and m is 2 or 3.

It is considered that the Co chelates of formula I are novel and inventive compounds in their own right.

There is therefore further provided according to the invention a CoII chelate complex of formula I as defined above and also the CoIII analogue of this complex as defined above.

The Co chelates of the invention are electrically neutral, the surrounding ligands providing a double negative charge to balance the $Co^{2+}$ charge. The negative charges are believed to be delocalised rather than being associated with any particular atoms.

Preferred specific cobalt chelates for use in the invention (formulae shown below) are CoII (bis 3,3'-dimethylbenzildioxime diborondifluoride) having the formula II, CoII (bis 2,2'-dimethylbenzildioxime diborondifluoride) having the formula III, CoII(bis 2,2',4,4'-tetramethylbenzildioxime diborondifluoride) having the formula IV, and, in particular, CoII (bis 4,4'-dimethylbenzildioxime dibrorondifluoride) which has the formula V:

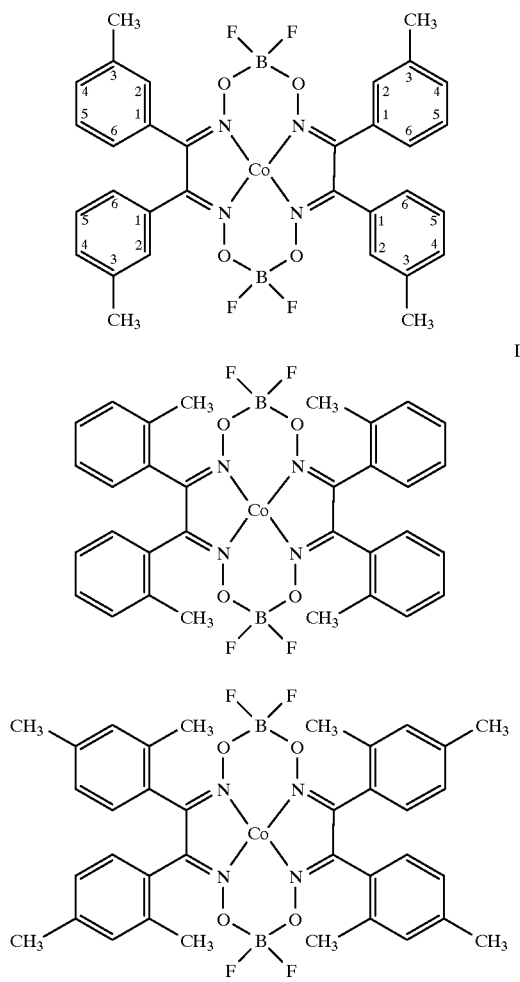

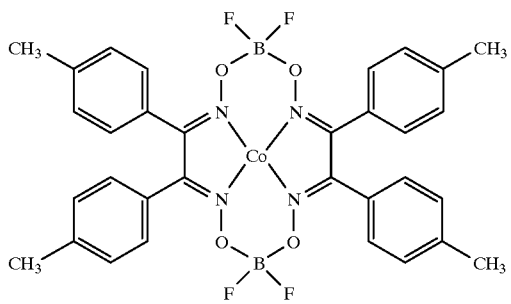

(The formula II above shows, for convenience, the direction of ring numbering employed generally herein for the compounds of formula I).

The Co chelates of the invention are all effective molecular weight control compounds when used in the invention process. Some of them, however, possess particularly surprising and useful properties in certain circumstances.

For example, the chelate compound of formula V is, most surprisingly, much more effective at lowering molecular weight in aqueous-based polymerisations (e.g. in both emulsion and suspension polymerisations), and is also a little more effective in the case of bulk or solution polymerisations, than the corresponding known compound in which all the rings are unsubstituted, i.e. CoII (bis benzildioxime diborondifluoride), i.e. having the formula V but with all the methyl groups replaced by H, such a chelate being disclosed in U.S. Pat. No. 4,679,4054 and perceived to be a very good CCTA catalyst in its own right. Thus it is possible to use a much smaller quantity of the compound of formula V to achieve a given lowering of molecular weight in (particularly) aqueous polymerisations than that of the unsubstituted compound. Alternatively, a greater lowering of molecular weight may be achieved using about the same amounts of the catalyst compounds.

Hence the compound of formula V is, surprisingly, an exceptionally useful and active all-round catalyst for lowering molecular weight (i.e. in solution and bulk polymerisation as well as, more particularly, in emulsion and suspension polymerisation).

With regard to invention Co chelates other than those of formula V, these are also useful and will all effect molecular weight reduction in organic solvent, bulk, and aqueous-based polymerisations (emulsion and suspension polymerisation) although their effectiveness will vary somewhat according to the reaction medium being employed (bulk, solvent, aqueous emulsion, or aqueous suspension) and the particular invention Co chelate which is used.

For example in the case of bulk polymerisation, the 3-methyl substituted analogue of the 4-methyl substituted compound, viz the compound of formula II, and also some of the higher alkyl homologues of the chelate of formula V, viz those where the methyl groups are replaced in each 4 phenyl position by ethyl (structure VI; formula not shown) and isopropyl (structure VII; formula not shown), were found by us to be a little more effective than the completely unsubstituted known compound mentioned above (i.e. Co II bis benzildioxime diborondifluoride). On the other hand, the performance of the 2-methyl analogue of compound V (structure III, formula shown above) was found to be somewhat worse than the completely unsubstituted compound in bulk polymerisation, while that of the 4-tert butyl analogue, (structure VIII, formula not shown) was found to be about the same.

In the case of aqueous suspension polymerisation we found that these other invention compounds (i.e. other than that of formula V, as mentioned above) also had significantly improved effectiveness in comparison to the unsubstituted Co chelate compound, apart from the 2-methyl compound of formula III which had about the same effectiveness as the unsubstituted compound (although this may have been due to the compound of formula III as used from its preparation being somewhat impure). In the case of aqueous emulsion polymerisation however, we found that the 2- or 3-methyl analogues of V (viz II and III) were usually more effective than the completely unsubstituted compound (although the results were variable in this respect), while the higher alkyl homologues of V, viz VI, VII and VIII (see above) were distinctly less effective than the completely unsubstituted compound—but nevertheless still caused reduced molecular weight in comparison to polymerisation in the absence of a Co catalyst.

With regard to the CoIII analogues of said compounds of said formulae, these arise when the Co is additionally bonded to a further atom, ion or organic group which is homolytically dissociable, such as H, optionally substituted $C_{1-10}$ alkyl, cyano, halide, ester, $C_{6-10}$ aryl (including heterocyclic $C_{6-10}$ aryl), and $C_{6-10}$ alicyclyl (including heterocyclic $C_{6-10}$ alicyclyl), such a further group usually being located in an axial position (i.e. perpendicular to the equatorial ligands shown in the formulae above). Preferred are the analogous CoII complexes in which the CoIII is reducible to CoII under the conditions of the polymerisation. Axial groups such as halogen and H may be particularly suitable. Other possible particularly suitable groups include axial alkyl groups (preferably 1 to 10 carbons) bearing one or more substituents on the carbon atoms bonded to the metal ion; such substitutents may include nitrile, ester, and optionally substituted aromatic groups. Some of these CoIII complexes may be stable materials under ordinary storage conditions, and may only react under the free-radical-generating conditions of the polymerisation process. Others, particularly where H is the further (axial) group, may be highly reactive intermediate species—and indeed it is possible that all the CoII complexes (and possibly the CoIII ones as well) exert their chain transfer effect by proceeding through the reactive CoIIIH intermediate. It is also possible that there is always a periodic interchange between the CoII and CoIII valency states in the complexes during the polymerisation. In fact the actual mechanism involved is complex and not properly understood on our part and we do not wish to be bound by any particular theory nor to an identification of the specific chemical constitution or valency state of the Co complex during the actual polymerisation process.

It is also possible for the cobalt complexes as defined above (i.e. CoII or CoIII complexes) to additionally have further ligands (normally one or two) coordinated to the Co atom (presumably axially), which do not alter the Co valency state. These may be derived en passant from the reaction medium used in the preparation of the Co complex or from the polymerisation medium used in the polymerisation process, or may be derived by deliberately adding a compound which will provide such ligands, and it is often the case that the coordinated presence thereof in the complex will ameliorate the latter's effectiveness. However, they are not essential to the invention, and for convenience they have not been shown in the various formulae written out above. Typical of such additional ligands are weakly basic tertiary amines such as pyridine (or their substituted derivatives), trialkyl amines, dialkylamines, ethers such as tetrahydrofuran and diethyl ether, alcohols such as methanol, and also optionally substituted trialkyl, triaryl or tri(alkyl-aryl) phosphines (or analogous compounds such as corresponding alkoxy or aryloxy phosphines). (Such alkyl or alkoxy groups preferably, and independently, have 1 to 10 carbons, and such aryl or aryloxy groups preferably, and independently, have 6 to 10 carbon atoms.) One or more water molecules could also be coordinated to the Co complex.

The defined cobalt chelate complexes allow the efficient production of oligomers and are considered to be functioning as chain transfer agents. As mentioned above, some members within the defined scope are exceptionally active in aqueous polymerisations. Generally speaking, the degree of polymerisation of such oligomers (overall in the case of copolymers) will usually be within the range 2 to about 500 (i.e. 2 to 500 polymerised units), preferably 2 to 300, and more preferably 5 to 200.

The polymerisation process can be carried out in the presence of a polymerisation medium (acting as a carrier medium for the components and as a heat transfer medium) or in the absence of such a medium (i.e. in bulk). When using a polymerisation medium, the polymerisation may be e.g. a solution (using organic solvent) polymerisation, an aqueous suspension or emulsion polymerisation, or a non-aqueous dispersion polymerisation. It is also possible to carry out the polymerisation process in the presence of a preformed polymer (such as a polyester or polyurethane) which may be dispersed in water or other dispersing medium to produce a composite of the preformed polymer and the product of the polymerisation process.

Typical organic solvents which may be used as the medium for the polymerisation include aromatic hydrocarbons such as benzene, toluene, and the xylenes; ethers such as diethyl ether, tetrahydrofuran, alkoxylated ethylene glycol or polyethyleneglycol; alcohols such as methanol, ethanol, propanol and butanol and their esters with carboxylic acids such as acetic, propionic and butyric acids, ketones such as acetone or methyl ethyl ketone; and liquid tertiary amines such as pyridine. Mixtures of solvents may be used.

Water may also be used as a polymerisation medium (sometimes in combination with a solvent(s), usually water-miscible, examples of which are described above) as in suspension or emulsion polymerisations and for such processes conventional emulsifying or suspension agents (stabilisers) may be employed.

Aqueous emulsion and suspension polymerisation techniques are in their basic format extremely well known and need not be described in great detail. Suffice to say that such processes involve dispersing the monomer(s) in an aqueous medium and conducting polymerisation using a free-radical initiator (often water soluble in the case of emulsion polymerisation, and often monomer soluble in the case of suspension polymerisation) and (usually) appropriate heating (e.g. 30 to 120° C., more usually 45 to 90° C.) and agitation (stirring) being employed. An aqueous emulsion polymerisation can be effected with conventional emulsifying agents (surfactants) being used [e.g. anionic and/or non-ionic emulsifiers such as Na, K and $NH_4$ salts of dialkylsulphosuccinates, Na, K and $NH_4$ salts of sulphated oils, Na, K and $NH_4$ salts of alkyl sulphonic acids, Na, K and $NH_4$ alkyl sulphates such as Na lauryl sulphate, alkali metal salts of sulphonic acids. $C_{12-24}$ fatty alcohols, ethoxylated fatty acids and/or fatty amides, and Na, K and $NH_4$ salts of fatty acids such as Na stearate and Na oleate; aryl-containing analogues of the alkyl-containing surfactants are also useful; other surfactants include phosphates and cationic compounds such as hexadecyltrimethyl ammonium bromide. Non-ionic emulsifiers based on ethoxylate chains may also be used. Further, emulsifiers having both ionic and non-ionic character may be used. The amount used is usually 0.2 to 15% by weight, more usually 0.3 to 5% by weight, based on the weight of total monomer(s) charged]. In the case of aqueous suspension polymerisation, protective colloids are usually employed as stabilisers, examples of which include partially hydrolysed polyvinyl acetate (varying degrees of hydrolysis), cellulose derivatives, polyvinyl pyrollidone, and polyacrylic acid. The amount used is usually 0.1 to 8%, more usually 0.1 to 5%, calculated on monomer weight. Salts such as $Na_2SO_4$ can be included for reducing monomer solubility in the aqueous phase and to improve stabilisation.

The polymerisations (i.e. in general, including bulk, solution, as well as aqueous suspension or emulsion polymerisation and non-aqueous dispersion polymerisation) are usually performed at a temperature within the range of 25 to 160° C. (more usually 45 to 90° C.). Any suitable free radical yielding initiator appropriate to the type of polymerisation process employed may be used in the process of the invention, the usual criteria being that it has acceptable solubility in one or more of the other polymerisation components (e.g. solvent, monomer(s), or water), is sufficiently active at the polymerisation temperature (usually having a half life within the range 0.5 to 5 hours), and does not unacceptably affect the stability for the Co chelate. Examples of such free-radical-yielding initiators include azo compounds such as 2,2'-azobis(isobutyronitrile) (AIBN), 2,2'-azobis-(2-methyl)butanenitrile, 4,4'-azobis(4-cyanaovaleric acid), 2-(t-butylazo)-2-cyanopropane, 2,2'-azobis[2-methyl-N-(1,1)-bis(hydroxyethyl)]-propionamide, and 2,2'-azobis[2-methyl-N-hydroxyethyl)]-propionamide. Other free radical initiators may also be used, examples of which include peroxy compounds such as benzoyl peroxide, lauroyl peroxide, hydrogen peroxide, and Na, K and $NH_4$ persulphates. Other useful peroxyinitiators include peroxyesters, particular examples of which are tert-butylperoxy-2-ethylhexanoate and tert-amylperoxy-2-ethylhexanoate. Redox initiator systems can also be used, examples of which include redox pairs such as $NH_4$ persulphate and Na metabisulphite, and tert-butylhydroperoxide (TPHPO) and iso-ascorbic acid. The amount of initiator will depend inter alia on the type of polymerisation (bulk, solution, aqueous emulsion, aqueous suspension or non-aqueous dispersion), but in general, will usually be within the broad range 0.05 to 15%, based on the weight of total monomer(s) charged. (An initiator, e.g. $NH_4$ persulphate may optionally be added at the end of polymerisation to remove residual monomer).

The use of the defined Co chelates as molecular weight control compounds in the invention process avoids the requirement to use conventional chain transfer agents which often have disadvantages of one sort or another. For example, mercaptans impart a pronounced odour, while halogenated hydrocarbons (such as bromoform or carbon tetrachloride) are environmentally suspect. In addition thiols are incompatible with certain monomers (such as glycidyl methacrylate) which are useful in applications such as crosslinkable powder coatings.

The defined Co chelates, acting to control molecular weight, may be used in a very low amount (because they act in a catalytic manner) in comparison to conventional chain transfer agents for achieving comparable molecular weight reduction. (Some can be used in an exceptionally low amount as mentioned above.) This allows a much purer product to be made.

The invention process may be carried out using an "all-in-one" batch process in which all components are present in the reaction medium at the start of polymerisation or a semi batch process in which one or more of the components employed (usually at least one of the monomers) is wholly or partially fed to the polymerisation medium during the polymerisation.

The chelates used in the process may be prepared beforehand or may be formed in situ from the appropriate reactants.

The amount of cobalt chelate used in the polymerisation process will depend upon the desired molecular weight of the oligomer to be produced and other factors including the monomer composition and polymerisation conditions being employed. Therefore the amount of cobalt chelate used may cover a wide range such that usually the mole ratio of monomer(s) to cobalt chelate will be within the range from 10,000,000/1 to 50/1 and more typically 1,000,000/1 to 5,000/1. In the polymerisation process the mole ratio of monomer(s) to free radical initiator will usually be within the broad range 4,000/1 to 10/1 and more typically 1,000/1 to 30/1.

The process of the invention is most effectively applied to the homo- and copolymerisation of methacrylate esters (copolymerisation being with any suitable comonomer(s), such as a different methacrylate ester or styrene) and also to the homo- and copolymerisation of styrenes (copolymerisation being with any suitable comonomer(s) such as a different styrene or a methacrylate ester). Acrylate esters can also be polymerised, particularly if included as comonomers with methacrylic esters and/or styrenes. The invention process has a particular utility in that it may be employed for the polymerisation of acid-functional monomers (which may e.g. be included as comonomer(s) in methacrylate ester or styrene copolymerisation).

Examples of monomers that may be polymerised include methyl methacrylate, ethyl methacrylate, butyl methacrylate (all isomers), and other alkyl methacrylates (e.g. up to 14 C atoms; corresponding acrylates; also functionalised methacrylates and acrylates including glycidyl methacrylate, trimethoxysilyl propyl methacrylate, allyl methacrylate, hydroxyethyl methacrylate, hydroxypropyl methacrylate, dialkylaminoalkyl methacrylates (alkyl preferably 1–4 carbons) and acetoacetoxy esters of hydroxyalkyl acrylates and methacrylates such as acetoacetoxyethylmethacrylate; fluoroalkyl (meth)acrylates; methacrylic acid, acrylic acid; fumaric acid (and esters), itaconic acid (and esters), maleic anhydride; styrene, α-methyl styrene and other styrene derivatives such as styrene-p-sulphonic acid and isomers thereof, 4-chlorostyrene and isomers thereof, and 4-bromostyrene and isomers thereof; vinyl halides such as vinyl chloride and vinyl fluoride; vinyl esters such vinyl as vinyl acetate; acrylonitrile, methacrylonitrile; vinylidene halides of formula $CH_2=C(Hal)_2$ where each halogen is independently Cl or F; optionally substituted butadienes of the formula $CH_2=C(R^2) C(R^2)=CH_2$ where $R^2$ is independently H, Cl to C10 alkyl, Cl, or F; sulphonic acids or derivatives thereof of formula $CH_2=CHSO_2OM$ wherein M is Na, K, Li, $N(R^3)_4$, $R^3$ or $—(CH_2)_2-D$ where each $R^3$ is independently H or C1–C10 alkyl, D is $CO_2G$, OH, $N(R^3)_4$ or $SO_2OG$ and G is H, Li, Na, K or $N(R^3)_4$, acrylamide or derivatives thereof of formula $CH_2=CHCON(R^3)_2$, and methacrylamide or derivatives thereof of formula $CH_2=C(CH^3{}_2)CON(R^3)_2$, and keto containing amides such as diacetone acrylamide. Mixtures of such monomers may be used, e.g. to form bi- or multicopolymers.

Preferred monomers are Cl-C10 alkyl methacrylates and acrylates, methacrylic acid and/or acrylic acid, styrene, styrene derivatives, hydroxy C1–C14 alkyl methacrylates and acrylates such as hydroxyethyl methacrylate and hydroxypropyl methacrylate, epoxy C1–C14 alkyl methacrylates and acrylates such as glycidyl methacrylate.

The oligomers made using the invention process employing the defined Co chelate catalysts are useful in a variety of applications.

They are particularly suitable for use in coatings applications in which they, or products derived from or including them, may provide a key part of the coating compositions or formulations being employed. Such coatings compositions which can be pigmented or unpigmented, include: waterborne coating compositions, particularly when the oligomer has been derived from aqueous emulsion polymerisation; organic solvent-borne coating compositions, particularly of high solids content; and powder coating compositions. Solvent-borne and powder coating compositions preferably employ oligomers made using an aqueous suspension or organic solvent solution polymerisation.

The coating compositions may be used for coating a variety of substrates, e.g. metals, wood, paper, board, cementitious materials, polymeric films or other plastics articles.

A further use for the oligomers made by the invention process is in graphics arts applications, wherein they, or products derived from them may provide important components of water- or solvent-based inks and overprint varnishes.

Yet a further use for the oligomers made by the invention process is in adhesives applications, wherein they, or products derived from them, may be employed in pressure sensitive, hot melt, contact and laminating adhesives compositions. Such adhesives compositions may be water-based, organic solvent-based, or of the hot-melt-type.

As mentioned supra, the invention process is particularly suitable for incorporating acid-functional monomers (such as methacrylic acid) into the oligomer. If present in sufficient amount, such a monomer will render the oligomer hydrophilic or even water-soluble when the acid groups are in salt form (e.g. by being neutralized). Such a water-dispersible or water-soluble oligomer has many uses—see e.g. the disclosure of WO95/04767, wherein a water-soluble oligomer is employed in the formation of a multi-phase polymer system in which an emulsion polymerisation to form a hydrophobic polymer is performed in the presence of the hydrophilic oligomer. Such multi-phase products have uses e.g. in water-based inks and overprint varnishes.

Also as mentioned supra, the invention process is very suitable for incorporating functionality into the oligomer, by means of using functional monomers as part of monomer system used for the oligomer. Examples of such functional monomers include allyl, glycidyl, or hydroxyalkyl (e.g. hydroxyethyl) methacrylates or acrylates, as well as keto-functional monomers such as the acetoacetoxy esters of hydroxyalkyl acrylates and methacrylates such as acetoacetoxyethyl methacrylate, and also keto-containing amides such as diacetone acrylamide. One of the purposes of using functional monomer is to provide subsequent crosslinkability in the resulting oligomer or polymer system derived from it.

The present invention is now illustrated but in no way limited by reference to the following examples. Unless otherwise specified all parts, percentages and ratios are on a weight basis. The prefix C before an example denotes that it is comparative.

In the example, the following abbreviations and terms are specified:

MMA: methyl methacrylate
MAA: methacrylic acid
STY: styrene
EMA: ethyl methacrylate
EA: ethyl acrylate
HPMMA: hydroxypropylmethylacrylate
GMA: glycidylmethacrylate
PMMA: polymethylmethacrylate
Me: methyl
Et: ethyl
iPr: isopropyl
tBu: tertiary butyl
AIBN: 2,2'-azobis(isobutyronitrile)
CVA: 4,4'-azobis(4-cyanovaleric acid)
BPO: benzoyl peroxide
CCTA: catalytic chain transfer agent
THF: tetrahydrofuran
CoPhBF: CoII (bis benzildioxime diborondifluoride)
Co4-MePhBF: CoII (bis 4,4'-dimethylbenzildioxime diborondifluoride)
Co3-MePhBF: CoII (bis 3,3'-dimethylbenzildioxime diborondifluoride)
Co2-MePhBF: CoII (bis 2,2'-dimethylbenzildioxime diborondifluoride)
Co4-EtPhBF: CoII (bis 4,4'-diethylbenzildioxime diborondifluoride)
Co4-iPrPhBF: CoII (bis 4,4,'-diisopropylbenzildioxime diborondifluoride)
Co4-tBuPhBF: CoII (bis 4,4'-ditertbutlylbenzil dioximediborondifluoride)
SLS: sodium lauryl sulphate
Mn: number average molecular weight
Mw: weight average molecular weight
PDi: Mw/Mn (polydispersity index)
Dowfax 2A1: anionic surfactant (supplied by Dow Chemical Co. as 50% aqueous solution)
GPC: gel permeation chromatography
MEK: methyl ethyl ketone General Procedures (i) Synthesis of Cobalt CCTAs All substituted benzils were prepared following the procedure taught in Org.Syn.CoII.Vol 1, page 87. All dioximes were prepared using the method described by Brady and Perry, JCS, 2874–2882, 1925.

The following general method was used to prepared the cobaloximes of the present invention, the method exemplifying here the preparation of various CoII compounds of formula I [with n=1 and X=alkyl in each benzene ring, and each Z=F] as typical:

The appropriate dialkylbenzildioxime (2 mol.equivs) was stirred together with cobaltacetate.tetrahydrate (1mol.equiv), and diethylether(approx. 70mol equiv.) under an atmosphere of deoxygenated dinitrogen. Borontrifluoride.etherate (10 mol equivs) was introduced dropwise over a period of 15 minutes, ensuring that the reaction temperature did not exceed 5° C. On completion of the addition the reaction mixture was held below 5° C. for a further 10 minutes. The mixture was then slowly heated to 40° C. and held at this temperature for 15–90 minutes. The mixture was then cooled to 0° C. and sodium carbonate (between 1.25 and 4 mol equivs) added. The mixture was stirred a further 30 minutes then methanol (approx 10 mol. equivs) added. The resulting solid was isolated by filtration, water washed to remove inorganics and finally washed with methanol (approx 20 mol. equivs) to yield the product as the dimethanol complex (Formula IX).

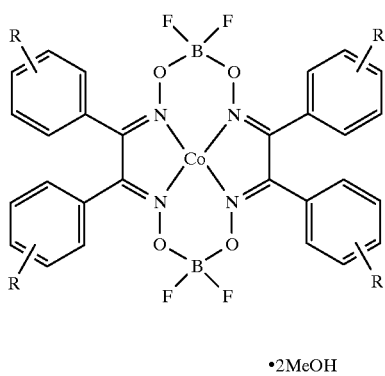

•2MeOH

The results are summarised in Table 1 below.

TABLE 1

| R in Formula IX | % Yield | % found Cobalt | % Theoretical Cobalt | Identification (in terms of integers of formula I with n = 1 in each ring) |
|---|---|---|---|---|
| 2-methyl | 52 | 7.1 | 7.8 | *III (X = 2-Me in each ring, each Z = F) |
| 3-methyl | 25 | 7.7 | 7.8 | **II (X = 3-Me in each ring, each Z = F) |
| 4-methyl | 96 | 7.7 | 7.5 | *V (X = 4-Me in each ring, each Z = F) |
| 4-ethyl | 13 | 7.6 | 7.5 | **VI (X = 4-Et in each ring, each Z = F) |
| 4-isopropyl | 26 | 6.5 | 6.8 | **VII (X = 4-iPr in each ring, each Z = F) |
| 4-t butyl | 46 | 5.1 | 6.4 | **VIII (X = 4-tBu in each ring, each Z = F) |

*formula written out above
**formula not written out (ii) Bulk Polymerisation

[The following procedure is written in terms of MMA homopolymerisations, but is equally applicable mutatis mutandis to the preparation of copolymers].

MMA was deoxygenated by bubbling nitrogen through it for at least 1 hour prior to use. An amount of CCTA was accurately weighed into a round bottomed flask. The flask was evacuated and filled with nitrogen at least three times. MMA was added via syringe to form a stock solution of the CCTA with a typical concentration of ca. $2 \times 10^{-4}$ mol $dm^{-3}$. AIBN (0.085g) was added to each of a number of Schlenck tubes which were then evacuated and filled with nitrogen at least three times. Varying aliquots of MMA and the CCTA stock solution were added to each Schlenck tube via syringe so that the total volume was 10 ml in each case and the mole ratio of CCTA/MMA was in the range 0 to $2.2 \times 10^{-6}$. Each tube was heated to 60° C. by means of a thermostatically controlled water bath. After half hour a sample was removed from each tube and quenched by addition to a solution of hydroquinone in THF. The molecular weight of the polymer formed was determined by GPC relative to PMMA standards.

(iii) Solution Polymerisation

To a 200 ml Schlenk tube filled with dry nitrogen and 0.085g AIBN were added the appropriate amounts of the monomers (typically 10 ml MMA) and 20 ml of the appropriate solvent, all of which had been previously sparged with dry nitrogen. The desired amount of cobalt catalyst was then added and the tube heated to 60° C. under nitrogen. A sample was removed after half an hour as described above for bulk polymerisation or sometimes after an hour.

(iv) Suspension Polymerisation

The following procedure was employed.

1) A 3 liter round bottomed glass reaction vessel, fitted with a water-cooled condenser, was purged with nitrogen for not less than 1 hour before starting the polymerisation.
2) Sodium sulphate (0.2 wt % based on total monomer) and polyacrylic acid (2 wt % based on total monomer of a 12.5 wt % solution in water) were added to the reaction vessel, followed by 1200 mls of distilled water. The mixture was agitated throughout by a stainless steel paddle stirrer.
3) Using a thermostatically controlled water bath the contents of the reaction vessel were heated to 70° C.
4) Selected monomwers totalling 400 g were weighed in to a stoppered vessel followed by an initiator (eg AIBN or BPO in the range 0.2–1 wt % based on total monomer) and CCTA (typically 15 to 100 wt ppm based on total monomer mass). The mixture was then transferred to the reaction vessel with continued agitation and resulted in a temperature drop. The temperature was raised to either 75° C. or 80° C. and was maintained at that value (+/−2° C.) throughout the reaction.
5) 10 ml of a 2.5 wt % aqueous solution of Airvol V540 (a partially hydrolysed polyvinyl acetate supplied by Air Products) was added to the reaction vessel one hour after the contents had reached 75° C.
6) Ammonium persulphate (0.125 wt % based on total monomer mass) was added two hours after the formation of hard beads in the reaction vessel. The temperature was then increased by 5° C. and maintained at that temperature. An equivalent amount of ammonium persulphate was added thirty minutes after the first addition. The reaction was allowed to proceed for a further thirty minutes.
7) The contents of the reactor were cooled to less than 32° C. The beads were separated from the water by filtration, washed with excess water and dried in an oven at ca. 40° C.
8) The molecular weight of the polymer formed was determined by GPC relative to PMMA standards.

(vi) Emulsion Polymerisation

All monomers and water were degassed (deoxygenated) by passing a stream of nitrogen through them for at least one hour before use. Polymerisations were carried out under a nitrogen atmosphere in a one liter, baffled round bottom flange flask fitted with a mechanical stirrer.

De-oxygenated, de-ionised water and surfactant were charged to the reaction vessel which was heated to 75° C. and stirred. A weighed amount of the cobalt CCTA was added to a separate flask. The flask was evacuated and flushed with nitrogen three times. The monomer(s) were added to the flask containing the CCTA and the CCTA dissolved with stirring.

CVA and a further small portion of de-ionised water (typically 30 g) were added to the reaction vessel. The solution of cobalt catalyst in monomer mixture was fed to the reaction vessel using a syringe attached to syringe pump at a linear rate over a period of either 1 or 2 hours. The temperature in the reaction flask was maintained at 75° C. during the feed time and for at least a further 4 hours before cooling to ambient temperature.

All molecular weights were measured by Gel Permeation Chromatography (GPC) with either $CHCl_3$ or THF as eluent, against PMMA standards unless otherwise indicated.

EXAMPLES 1 TO 8, C9, C10

Bulk Polymerisations

The general procedure described above for bulk homopolymerisation of MMA was followed and representative results are given in Table 2. Mn's are those after 0.5 hours polymerisation. [MMA]/[Co] denotes the relative amounts of monomer (MMA) and Co catalyst on a molar basis.

TABLE 2

| Example** | Co CCTA | Structure or Formula* | [MMA]/[Co] | Mn |
|---|---|---|---|---|
| 1 | Co4-MePhBF | V | 794,000 | 3,217 |
| 2 | Co4-MePhBF | V | 781,000 | 3,101 |
| 3 | Co4-MePhBF | V | 776,000 | 2,889 |
| 4 | Co3-MePhBF | II | 768,000 | 2,749 |
| 5 | Co2-MePhBF | III | 781,000 | 4,899 |
| 6 | Co4-EtPhBF | VI | 800,000 | 2,911 |
| 7 | Co4-iPrPhBF | VII | 781,000 | 3,104 |
| 8 | Co4-tBuPhBF | VII | 810,000 | 3,888 |
| C9 | CoPhBF | | 800,000 | 3,920 |
| C10 | none | | — | 102,828 |

*where written
**Examples 1,2 and 3 were different polymerisations.

It will be noted that for the most part, the invention catalysts were more effective (at approximately the same Co catalyst level relative to monomer) in bulk polymerisation than the corresponding unsubstituted CoPhBF; the exceptions were Co4-t-BuPhBF which had about the same effectiveness in reducing molecular weight and Co2-MePhBF which was not as good as CoPhBF (although it was still effective as a CCTA).

EXAMPLES C11 TO C13, 14 TO 16

Solution Polymerisation

The general procedure for solution homopolymerisation of MMA described above was followed and the results are given in Table 3. Number average molecular weights (Mn) are indicated after 1 hour. [MMA]/[Co] denotes the relative amounts of mer (MMA) and catalyst on a molar basis.

TABLE 3

| Example | Catalyst | Solvent | [MMA]/[Co] | Mn |
|---|---|---|---|---|
| C11 | CoPhBF | MEK | 400,000 | 1,759 |
| C12 | CoPhBF | MEK | 600,000 | 2,303 |
| C13 | CoPhBF | MEK | 800,000 | 3,000 |
| 14 | Co4-MePhBF | MEK | 200,000 | 961 |
| 15 | Co4-MePhBF | MEK | 400,000 | 1,470 |
| 16 | Co4-MePhBF | MEK | 600,000 | 1,967 |

It was found that the invention Co CCTA Co4-MePhBF was a little more effective in MEK solution than the corresponding unsubstituted compound CoPhBF at the same catalyst levels relative to monomer.

EXAMPLES 17 TO 19, C20

Solution Polymerisation

In this example styrene was homopolymerised in MEK solvent according to the general procedure described above. Mn's were determined after 0.5 hours.

The results are given in Table 4.

TABLE 4

| Example | Catalyst | Solvent | [STY]/[Co] | Mn |
|---|---|---|---|---|
| 17 | Co4-MePhBF | MEK | 10,000 | 2,035 |
| 18 | Co4-MePhBF | MEK | 50,000 | 8,494 |
| 19 | Co4-MePhBF | MEK | 100,000 | 11,154 |
| C20 | none | MEK | — | 21,131 |

The invention CCTA used was thus found to be effective in controlling molecular weight during styrene polymerisations.

It may be mentioned that the polymerisation in bulk and solution exemplified above, where molecular weights were measured after 0.5 or 1 hour, may be allowed to proceed to high conversion while still achieving similar molecular weight reduction.

EXAMPLES 21 TO 27, C28 TO C30, 31 TO 36, C37, 38 TO 43

Emulsion Polymerisation

The general procedure for emulsion polymerisations was followed. Results are shown in Table 5 below. The results demonstrate the exceptional activity of Co4-MePhBF in aqueous emulsion polymerisation, with a clear advantage in comparison to the unsubstituted catalyst CoPhBF. The catalyst$ Co3-MePhBF and Co2-MePhBF were also effective in reducing molecular weight but less so than Co4-MePhBF and being rather variable in effect (usually more effective than CoPhBF but on one occasion for the 3-Me isomer, less so). The higher homologues however (viz Co4-EtPhBF, Co4-iPrPhBF and Co4-tBuPhBF) while still providing molecular weight reduction in emulsion polymerisation were considerably less effective than Co4-MePhBF (and also CoPhBF for that matter).

TABLE 5

| Ex No | Mass Water (g) | Mass Initiator CVA (g) | Surfactant | Wt % Surfactant (active based on monomers) | Total Mass Monomers (g) | MMA | MAA | STY | CCTA | CCTA Amount (ppm on a molar basis relative to monomer) | Feed Time Mins | Mn | Mw | PDi |
|---|---|---|---|---|---|---|---|---|---|---|---|---|---|---|
| MMA homopolymerisations | | | | | | | | | | | | | | |
| 21 | 290 | 1.65 | Dowfax 2A1 | 3.15 | 130 | 100 | 0 | 0 | Co4-MePhBF | 50 | 60 | 3790 | 14289 | 3.77 |
| 22 | 290 | 1.65 | Dowfax 2A1 | 3.15 | 130 | 100 | 0 | 0 | Co4-MePhBF | 100 | 60 | 1842 | 7234 | 3.93 |
| 23 | 290 | 1.65 | Dowfax 2A1 | 1.50 | 130 | 100 | 0 | 0 | Co2-MePhBF | 50 | 60 | 5214 | 12690 | 2.43 |
| 24 | 290 | 1.65 | Dowfax 2A1 | 1.50 | 130 | 100 | 0 | 0 | Co3-MePhBF | 50 | 60 | 6377 | 17562 | 2.75 |
| 25 | 290 | 1.65 | Dowfax 2A1 | 1.50 | 130 | 100 | 0 | 0 | Co4-EtPhBF | 50 | 60 | 57195 | 163476 | 2.86 |
| 26 | 290 | 1.65 | Dowfax 2A1 | 1.50 | 130 | 100 | 0 | 0 | Co4-iPrPhBF | 50 | 60 | 130572 | 308988 | 2.37 |
| 27 | 290 | 1.65 | Dowfax 2A1 | 1.50 | 130 | 100 | 0 | 0 | Co4-tBuPhBF | 50 | 60 | 56217 | 140767 | 2.50 |
| C28 | 450 | 2.10 | SLS | 2.10 | 200 | 100 | 0 | 0 | CoPhBF | 51 | 80 | 16658 | 38835 | 2.33 |
| C29 | 450 | 2.10 | SLS | 2.10 | 200 | 100 | 0 | 0 | CoPhBF | 102 | 60 | 8686 | 23986 | 2.76 |
| C30 | 290 | 1.65 | SLS | 2.00 | 130 | 100 | 0 | 0 | None | — | 60 | 164941 | 513444 | 3.11 |

TABLE 5-continued

| Ex No | Mass Water (g) | Mass Initiator CVA (g) | Surfactant | Wt % Surfactant (active based on monomers) | Total Mass Monomers (g) | Monomer Proportions MMA | Monomer Proportions MAA | Monomer Proportions STY | CCTA | CCTA Amount (ppm on a molar basis relative to monomer) | Feed Time Mins | Mn | Mw | PDi |
|---|---|---|---|---|---|---|---|---|---|---|---|---|---|---|
| MMA/MAA copolymerisations | | | | | | | | | | | | | | |
| 31 | 290 | 1.65 | Dowfax 2A1 | 3.15 | 130 | 70 | 30 | 0 | Co4-MePhBF | 51 | 60 | 3479 | 8263 | 2.38 |
| 32 | 290 | 1.65 | SLS | 3.20 | 130 | 70 | 30 | 0 | Co4-MePhBF | 75 | 60 | 2785 | 6259 | 2.25 |
| 33 | 290 | 1.65 | Dowfax 2A1 | 1.50 | 130 | 70 | 30 | 0 | Co2-MePhBF | 50 | 60 | 17640 | 29635 | 1.68 |
| 34 | 290 | 1.65 | Dowfax 2A1 | 1.50 | 130 | 70 | 30 | 0 | Co3-MePhBF | 50 | 60 | 36630 | 68626 | 1.87 |
| 35 | 290 | 1.65 | Dowfax 2A1 | 1.50 | 130 | 70 | 30 | 0 | Co4-iPrPhBF | 100 | 60 | 93067 | 257048 | 2.76 |
| 36 | 290 | 1.65 | Dowfax 2A1 | 1.50 | 130 | 70 | 30 | 0 | Co4-tBuPhBF | 100 | 60 | 60720 | 147448 | 2.43 |
| C37 | 450 | 2.54 | SLS | 1.50 | 200 | 70 | 30 | 0 | CoPhBF | 51 | 60 | 24627 | 53953 | 2.19 |
| 38 | 290 | 1.65 | Dowfax 2A1 | 1.50 | 130 | 40 | 30 | 30 | Co4-MePhBF | 100 | 120 | 2176 | 6880 | 3.16 |
| 39 | 290 | 1.65 | Dowfax 2A1 | 1.50 | 130 | 40 | 30 | 30 | Co2-MePhBF | 100 | 120 | 3682 | 11746 | 3.19 |
| 40 | 290 | 1.65 | Dowfax 2A1 | 1.50 | 130 | 40 | 30 | 30 | Co3-MePhBF | 100 | 120 | 27730 | 113424 | 4.09 |
| 41 | 290 | 1.65 | Dowfax 2A1 | 1.50 | 130 | 40 | 30 | 30 | Co4-EtPhBF | 100 | 120 | 56696 | 130593 | 2.30 |
| 42 | 450 | 1.65 | Dowfax 2A1 | 1.50 | 130 | 40 | 30 | 30 | Co4-iPrPhBF | 100 | 120 | 91508 | 264476 | 2.89 |
| 43 | 450 | 1.65 | Dowfax 2A1 | 1.50 | 130 | 40 | 30 | 30 | Co4-tBuPhBF | 100 | 120 | 57955 | 263570 | 4.55 |

EXAMPLES 44 TO 55, C56 TO C60, 61 TO 63
Suspension Polymerisation

The general procedure for suspension polymerisation described above was followed and the results shown in Table 6.

In most cases the experiments were duplicated to check consistency. All the CCTA's of the invention tested were found to be highly effective in aqueous suspension polymerisation at reducing molecular weight in homopolymerisations of MMA and copolymerisations containing BMA and MM using AIBN initiator (compare Example C56 which has an absence of CCTA and Examples 44–55 using the CCTA's of the invention). The amount of each CCTA used in Examples 46–55 was equivalent on a molar basis such that in these examples the mole ratio of MMA/CCTA was ca 300,000. It can readily be seen that with the exception of Co2-MePhBF (III) in Examples 54 and 55 the molecular weights in Examples 46–55 are very similar indicating similar chain transfer activity for each CCTA. The results for Co4-MePhBF do appear to be the best in aqueous suspension polymerisation even if not by much. The lower degree of molecular weight reduction when using Co2-MePhBF (III) is in line with the lower value obtained in bulk polymerisations and may in both cases possibly be related to its lower purity.

Comparisons with CoPhBF were provided in Examples C57–C60. With the exception of Co2-MePhBF (III) the molecular weight reductions were significantly greater when using the CCTA's of the invention than when using CoPhBF, i.e. an average Mn of ca. 2,400 compared to 5,500. Two different batches of CoPhBF prepared several months apart and at different sites were used in examples C57–C60 to ensure that the data was genuine and thus substantiate that higher Mn's were obtained with CoPhBF than with Co4-MePhBF at the same molar level and using the same monomer system and the same free radical initiator (AIBN).

Examples 44, 45 demonstrate that effective molecular weight reduction in aqueous suspension polymerisation can be achieved using termonomer systems ( MMA/BMA/MAA), although the molecular weight reduction was not so great as when using MMA alone (other conditions being comparable).

A few examples (Examples 61–63) were performed using BPO as the free radical initiator to demonstrate utility with a non-azo initiator.

TABLE 6

| Ex No | CCTA | CCTA Amount (ppm on wt basis relative to monomers) | Monomer Composition MMA | Monomer Composition BMA | Monomer Composition MAA | AIBN wt % | BPO wt % | Temperature °C. | Mn | Mw |
|---|---|---|---|---|---|---|---|---|---|---|
| AIBN Initiator | | | | | | | | | | |
| 44 | Co4-MePhBF | 25 | 67 | 35 | 8 | 0.2 | — | 75 | 3795 | 9600 |
| 45 | Co4-MePhBF | 25 | 60 | 32 | 8 | 0.2 | — | 75 | 5391 | 10198 |
| 46 | Co4-MePhBF | 25 | 100 | — | — | 0.5 | — | 75 | 2105 | 5112 |
| 47 | Co4-MePhBF | 25 | 100 | — | — | 0.5 | — | 75 | 1834 | 3952 |
| 48 | Co3-MePhBF | 25 | 100 | — | — | 0.5 | — | 75 | 2522 | 5041 |
| 49 | Co3-MePhBF | 25 | 100 | — | — | 0.5 | — | 75 | 2757 | 5499 |
| 50 | Co4-iPrPhBF | 29 | 100 | — | — | 0.5 | — | 75 | 2476 | 5479 |
| 51 | Co4-iPrPhBF | 29 | 100 | — | — | 0.5 | — | 75 | 2058 | 5175 |
| 52 | Co4-tBuPhBF | 31 | 100 | — | — | 0.5 | — | 75 | 2655 | 4629 |
| 53 | Co4-tBuPhBF | 31 | 100 | — | — | 0.5 | — | 75 | 2524 | 4907 |
| 54 | Co2-MePhBF | 25 | 100 | — | — | 0.5 | — | 75 | 5433 | 15957 |
| 55 | Co2-MePhBF | 25 | 100 | — | — | 0.5 | — | 75 | 4134 | 12001 |

TABLE 6-continued

| Ex No | CCTA | CCTA Amount (ppm on wt basis relative to monomers) | Monomer Composition MMA | BMA | MAA | AIBN wt % | BPO wt % | Temperature °C. | Mn | Mw |
|---|---|---|---|---|---|---|---|---|---|---|
| Comparative Examples | | | | | | | | | | |
| C56 | None | 0 | 100 | — | — | 0.5 | — | 75 | 137529 | 615220 |
| C57 | CoPhBF | 22 | 100 | — | — | 0.5 | — | 75 | 6809 | 17457 |
| C58 | CoPhBF | 22 | 100 | — | — | 0.5 | — | 75 | 4777 | 12427 |
| C59 | CoPhBF | 22 | 100 | — | — | 0.5 | — | 75 | 5306 | 13876 |
| C60 | CoPhBF | 22 | 100 | — | — | 0.5 | — | 75 | 5203 | 13909 |
| BPO Initiator | | | | | | | | | | |
| 61 | Co4-MePhBF | 50 | 92 | — | 8 | — | 1 | 80 | 6626 | 22183 |
| 62 | Co4-MePhBF | 50 | 100 | — | — | — | 1 | 80 | 5786 | 14287 |
| 63 | Co4-MePhBF | 50 | 100 | — | — | — | 1 | 80 | 5096 | 13260 |

We claim:

1. Process for the free-radical polymerisation of olefinically unsaturated monomer(s) using a free-radical initiator, the polymerisation being performed in the presence of a compound for effecting molecular weight-control, wherein the molecular weight control compound is a Co II chelate of the following formula I

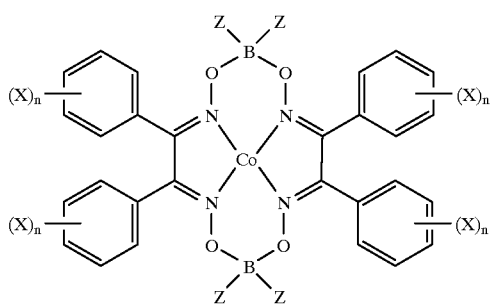

wherein each group X, independently in each ring and in different rings, is a substituent selected from alkyl of 1 to 14 carbon atoms and cycloalkyl of 6 to 14 carbon atoms; n, independently in each ring, is 0 to 5 provided that in at least one ring, n is 1 to 5; Z, independently on each boron atom, is selected from F, Cl, Br, OH, alkoxy of 1 to 12 carbon atoms, aryloxy of 6 to 12 carbon atoms, alkyl of 1 to 12 carbon atoms, and aryl of 6 to 12 carbon atoms;

or two Z groups taken together provide on one or both boron atoms a group —O—(Q)—O— where Q is a divalent aryl or alicyclic linking group or an alkylene linking group, or two Z groups taken together on one or both boron atoms provide a 1,5-cyclooctanediyl linking group;

or being a Co III analogue of said Co II chelate of formula I in which the Co atom is additionally covalently bonded, in a direction at right angles to the macrocyclic chelate ring system, to H, halide or other anion, or a homolytically dissociable organic group;

and wherein optionally at least one further ligand is coordinated to the Co II or Co III atom, being a ligand(s) which does not alter the Co valency state.

2. Process according to claim 1 wherein X is alkyl of 1 to 4 carbon atoms.

3. Process according to claim 2 wherein X is selected from methyl, ethyl, isopropyl and tert butyl.

4. Process according to claim 1 wherein n is 1 to 3 in each ring.

5. Process according to claim 1 wherein n has the same value in each ring.

6. Process according to claim 1 wherein n=1 or 2 in each ring.

7. Process according to claim 1 wherein X is methyl in each ring and n=1 in each ring.

8. Process according to claim 1 wherein X is the same in each ring and is selected from ethyl, isopropyl and tert butyl and n=1 in each ring.

9. Process according to claim 8 wherein X is in the 4 position in each ring.

10. Process according to claim 8 wherein X is in the same position in each ring and is in either the 2 or the 3 position.

11. Process according to claim 1 wherein each Z is F.

12. Process according to claim 1 in which the Co II chelate has n=1 in each ring, X is methyl in each ring and located in the 4 position of each ring, and each Z is F.

13. Process according to claim 1 in which the Co II chelate has n=1 in each ring, X is methyl in each ring and located in the 3 position of each ring, and each Z is F.

14. Process according to claim 1 in which the Co II chelate has n=1 in each ring, X is methyl in each ring and located in the 2 position of each ring, and each Z is F.

15. Process according to claim 1 wherein said polymerisation process is an aqueous suspension polymerisation process.

16. Process according to any one of claims 1 to 14 wherein said polymerisation process is an aqueous emulsion polymerisation process.

17. Process according to any one of claims 1 to 14 wherein said polymerisation process is a bulk polymerisation process.

18. Process according to any one of claims 1 to 14 wherein said polymerisation process is a solution polymerisation process in organic solvent.

19. Process according to any one of claims 1 to 14 wherein said polymerisation process is a non-aqueous dispersion polymerisation process.

20. Process according to claim 1 wherein said polymerisation process is carried out in the presence of a preformed polymer, preferably a polyester or a polyurethane.

21. Process according to claim 1 wherein said process is applied to the homo- or copolymerisation of methacrylate esters, the copolymerisation being with a different methacrylate ester and/or styrene or to the homo- or copolymerisation of styrenes, the copolymerisation being with a different styrene and/or a methacrylate ester.

22. Process according to claim 21 wherein the monomer system employed includes an acrylate ester(s).

23. Process according to claim 1 wherein the monomer system employed includes an acid-functional monomer.

24. Process according to claim 1 wherein said monomer (s) polymerised at least one selected from the group consisting of $C_{1-10}$ alkyl (meth)acrylates hydroxy $C_{1-14}$ alkyl (meth)acrylates, epoxy $C_{1-10}$ alkyl (meth)acrylates methacrylic acid, acrylic acid, styrene α-methylstyrene, styrene-p-sulphonic acid or isomers thereof, 4-bromostyrene or isomers thereof, and 4-chlorostyrene or isomers thereof.

25. Process according to claim 1 wherein the monomer polymerised is at least one selected from the group consisting of methyl methacrylate; ethyl methacrylate; n-propyl or i-propyl (meth)acrylate all isomers of butyl (meth)acrylate; glycidyl methacrylate; trimethoxysilylpropyl methacrylate; allyl methacrylate; hydroxyethyl methacrylate; hydroxypropyl methacrylate; dialkylaminoalkyl methacrylates; acetoacetoxy ethyl methacrylate; fluoroalkyl (meth)acrylates; methacrylic acid; acrylic acid; fumaric acid or esters thereof; itaconic acid or esters thereof; maleic anhydride; styrene; α-methyl styrene; vinyl chloride; vinyl fluoride; vinyl acetate; acrylonitrile; methacrylonitrile; vinylidene halides of formula $CH_2=C(Hal)_2$ where each halogen is independently Cl or F; butadienes of the formula $CH_2=C(R^2)C(R^2)=CH_2$ where $R^2$ is independently H, $C_1$ to $C_{10}$ alkyl, Cl, or F; $CH_2=CHSO_2OM$ wherein M is Na, K, Li, $N(R^3)_4$, $R^3$, or $—(CH_2)_2—D$ where each $R^3$ is independently H or $C_1$ to $C_{10}$ alkyl, D is $CO_2G$, OH, $N(R^3)_2$ or $SO_2OG$ and G is H, Li, Na, K or $N(R^3)_4$; $CH_2=CHCON(R^3)_2$, $CH_2=C(CH_3)CON(R^3)_2$; and diacetone acrylamide.

26. A Co II chelate of the following formula I:

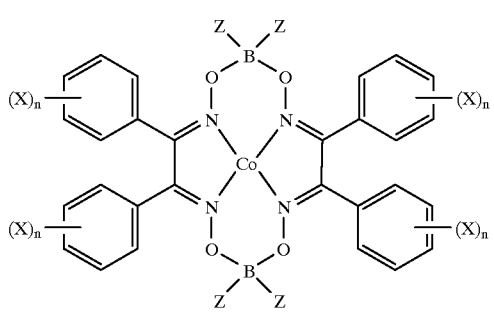

wherein each group X, independently in each ring and in different rings, is a substituent selected from alkyl of 1 to 14 carbon atoms and cycloalkyl of 6 to 14 carbon atoms; n, independently in each ring, is 0 to 5 provided that in at least one ring, n is 1 to 5; Z, independently on each boron atom, is selected F, Cl, Br, OH, alkoxy of 1 to 12 carbon atoms, aryloxy of 6 to 12 carbon atoms, alkyl of 1 to 12 carbon atoms, and aryl of 6 to 12 carbon atoms;

or two Z groups taken together provide on one or both boron atoms a group —O—(Q)—O— where Q is a divalent aryl or alicyclic linking group or an alkylene linking group, or two Z groups taken together on one or both boron atoms provide a 1,5-cyclooctanediyl linking group;

or being a Co III analogue of said Co II chelate of formula I in which the Co atom is additionally covalently bonded, in a direction at right angles to the macrocyclic chelate ring system, to H, halide or other anion, or a homolytically dissociable organic group; and wherein optionally at least one further ligand is coordinated to the Co II or Co III atom, being a ligand(s) which does not alter the Co valency state.

27. A Co II chelate according to claim 26 wherein X is alkyl of 1 to 4 carbon atoms.

28. A Co II chelate according to claim 27 wherein X is selected from methyl, ethyl, isopropyl, and tert butyl.

29. A Co II chelate according to any one claims 26 to 28 wherein n is 1 to 3 in each ring.

30. A Co II chelate according to any one of claims 26 to 28 wherein n has the same value in each ring.

31. A Co II chelate according to any one of claims 16 to 28 wherein n=1 or 2 in each ring.

32. A Co II chelate according to claim 26 where X is methyl in each ring and n=1 in each ring.

33. A Co II chelate according to claim 26 wherein X is the same in each ring and is selected from the group consisting of ethyl, isopropyl, and tert butyl, and n=1 in each ring.

34. A Co II chelate according to claim 33 wherein X is in the 4 position in each ring.

35. A Co II chelate according to claim 33 wherein X is in the same position in each ring and is in either the 2 or the 3 position.

36. A Co II chelate according to claim 26 wherein each Z is F.

37. A Co II chelate having the following formula V:

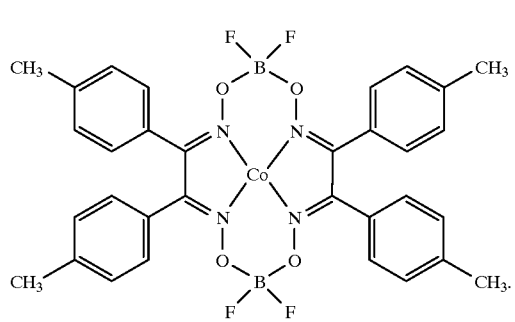

38. A Co II chelate having the following formula II:

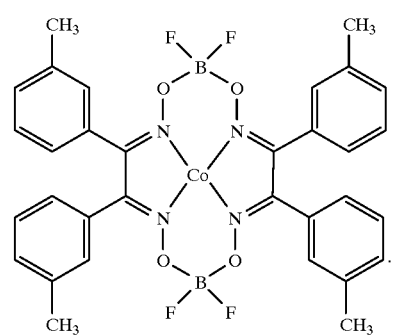

39. A Co II chelate having the following formula III:

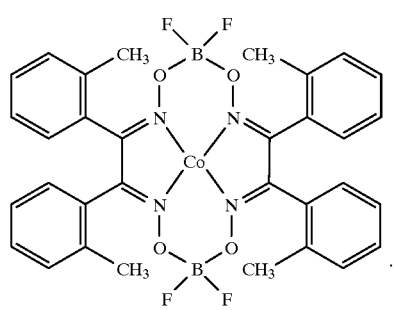

III

40. A Co chelate according to any one of claims 37 to 39 wherein the molecular weight control compound is the Co III analogue of said Co II chelate in which the Co atom is additionally bonded, in a direction at right angles to the macrocyclic ring system, to H, a halide, an anion, or a homolytically dissociable organic group.

41. A Co chelate according to any one of claims 37 to 39 wherein the Co chelate has at least one further ligand coordinated to the Co atom which does not alter its valency state.

42. Process for the production of a Co II chelate of formula I in which each Z is F, which comprises
   a) reacting a benzene-substituted benzil dioxime, which substitution corresponds with the desired substitution in the finished product, with cobalt acetate using diethyl ether as solvent and under an atmosphere of deoxygenated nitrogen ensuring that the reaction temperature does not exceed 5° C.,
   b) introducing boron trifluoride etherate dropwise to the reaction mixture, ensuring that the reaction temperature does not exceed 5° C.,
   c) warming the mixture to 40° C. and holding at this temperature to ensure reaction,
   d) cooling the reaction temperature to 0° C.,
   e) adding a base,
   f) stirring for a further period and then adding methanol,
   g) isolating the product by filtration, water wash, and then methanol wash, thereby to yield the Co-chelate as the dimethanol complex.

43. Process according to claim 6 wherein n is 1 in each ring.

44. Process according to claim 3 wherein X is methyl.

* * * * *